United States Patent [19]

Hutchins

[11] 4,185,617
[45] Jan. 29, 1980

[54] MAGNETICALLY DRIVEN CARDIAC-ASSIST PUMP SYSTEM

[76] Inventor: Thomas B. Hutchins, 310 NW. Brynwood La., Portland, Oreg. 97220

[21] Appl. No.: 900,474

[22] Filed: Apr. 27, 1978

[51] Int. Cl.[2] ............................ A61M 1/03; A61F 1/24
[52] U.S. Cl. ........................................ 128/1 D; 3/1.7; 417/420
[58] Field of Search ................ 128/1 D, 1.3, 230; 3/1, 1.7; 416/3; 417/234, 412, 420, 477, 505

[56] References Cited

U.S. PATENT DOCUMENTS

| 3,513,486 | 5/1970 | DeBennetot et al. | 417/420 |
|---|---|---|---|
| 3,791,769 | 2/1974 | Kovacs | 3/1.7 |
| 4,004,299 | 1/1977 | Runge | 128/1 D |
| 4,051,840 | 10/1977 | Kantrowitz et al. | 128/1 D |
| 4,058,855 | 11/1977 | Runge | 128/1D |
| 4,135,253 | 1/1979 | Reich et al. | 128/1 D |

*Primary Examiner*—Robert W. Michell
*Assistant Examiner*—C. F. Rosenbaum
*Attorney, Agent, or Firm*—Kolisch, Hartwell, Dickinson & Stuart

[57] ABSTRACT

A magnetically driven pump system designed for use with a body-implantable heart-assist device. The system includes a body-implantable bellows-type pump adapted to transfer fluid to and from the heart-assist device, and a driving unit effective to drive the pump by magnetic coupling across the surface of the body.

4 Claims, 7 Drawing Figures

U.S. Patent           Jan. 29, 1980           4,185,617
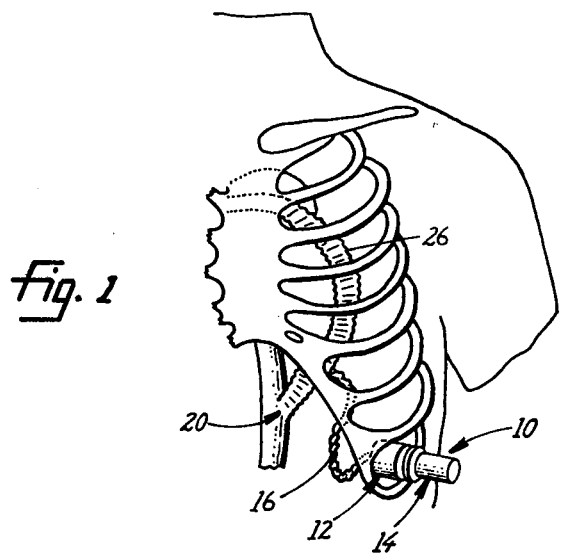
Fig. 1
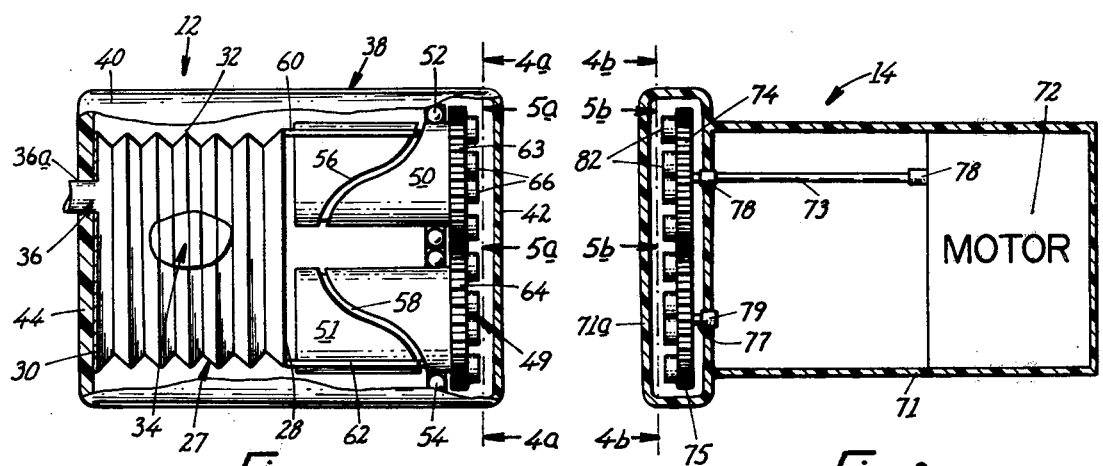
Fig. 2
Fig. 3
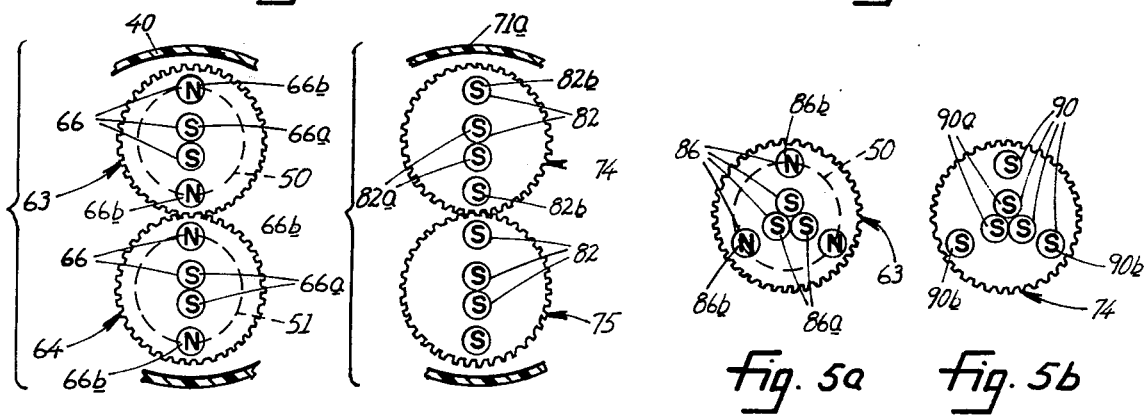
Fig. 4a    Fig. 4b    Fig. 5a    Fig. 5b

MAGNETICALLY DRIVEN CARDIAC-ASSIST PUMP SYSTEM

BACKGROUND AND SUMMARY

The present invention relates to a cardiac-assist pump system, and in particular, to such a system having a body-implantable pump which is drivable by magnetic coupling across a body surface.

Body-implantable heart assist devices are employed in the treatment of acute heart conditions in which it is necessary to augment the pumping capacity of the heart. Such devices generally include an inflatable balloon positioned within a circulatory pumping chamber. The pumping chamber may be surgically placed intraaortically, or placed across the heart interaortically. The volume of the pumping chamber is alternately increased and decreased by inflating and evacuating the balloon, causing blood to be pumped through the chamber. The balloon is alternately and recurrently inflated and deflated by a fluid pump located external the body. This pump may be connected to the balloon by a tube that passes, transcutaneously, from pump to balloon.

Because heart-assist devices of this type are simple, lightweight, and can be constructed of biologically inert material, operative and post-operative complications can be minimized. However, a significant disadvantage of the above-described kind of device is the need for a transcutaneous, fluid-carrying tube connecting the implanted heart assist device and the external pump.

Problems associated with transcutaneous tubes are well-known in medicine. It is frequently necessary to employ such tubes in draining infection, or where there is a need to obtain frequent intravenous access, such as in kidney dialysis. Because of susceptability to infection, the wounds surrounding the exiting tube must be kept virtually germ free. Further, the exiting tube must be substantially immobilized against the skin to prevent chronic irritation of the wound. Although certain types of puncturable skin coverings have been developed to protect a transcutaneous wound, the above-described problems of infection and irritation have not been satisfactorily solved to data.

In view of the above, the advantages of a heart-assist pump system which does not employ external wire or tube connections are evident.

It is, therefore, an object of the present invention to provide a simple, efficient body-implantable heart-assist pumping system not requiring transcutaneous wires or tubes.

Specifically, it is an object of the invention to provide a heart-assist pump system which is drivable by magnetic coupling across the surface of the body.

It is yet another object of the invention to provide such a system which is lightweight, constructed of biocompatible material, and relatively inexpensive in manufacture.

The present invention provides a body-implantable bellows-type pump which designed to be connected to a conventional heart-assist device employing an inflatable balloon, as described above. The bellows pump, the balloon and a tube connecting the two form a body-implantable closed system operative to transfer a fluid, such as air, alternately and recurrently between the bellows pump and the balloon. The bellows pump includes a movable pumping wall and a pair of rotary magnetic elements which are coupled thereto by cylindrical cams which effect reciprocation of the bellows pumping wall upon rotation of the magnetic elements. A pair of motor-driven rotary magnetic elements placed close to the surface of a body, are adapted to rotate, by magnetic coupling across such surface, the pump rotary magnetic elements, thus to operate the implanted pump and associated heart-assist device.

These and other objects and features of the present invention all now be more fully described with reference to the following detailed description of a preferred embodiment of the invention and the accompanying drawings.

DRAWINGS

FIG. 1 is a diagramatic representation of a magnetically-coupled pumping system constructed according to an embodiment of the present invention, shown in combination with a heart-assist pumping device—all in relation to a person's body;

FIG. 2 is an enlarged cutaway side view of a bellows-type pump constructed in accordance with the present invention;

FIG. 3 is an enlarged, cutaway, partially diagrammatic side view of a unit used to drive the pump of FIG. 2;

FIGS. 4a and 4b are fragmentary sectional views taken generally along lines 4a–4a of FIG. 2, and 4b–4b of FIG. 3, respectively; and FIGS. 5a and 5b are sectional views taken generally along lines 5a–5a and 5b–5b, respectively, but showing an alternate arrangement of magnetic arrays used in coupling the unit of FIG. 3 to the pump of FIG. 2.

DETAILED DESCRIPTION OF PREFERRED EMBODIMENTS OF THE INVENTION

Referring now to FIG. 1, there is shown at 10 a magnetically-coupled pumping device constructed according to a preferred embodiment of the present invention, generally including a body-implantable pump 12 and a pump driving unit 14. Pump 12 is connected by a tube 16 to a body-implanted heart-assist device 20, shown here connected intraaortically across the heart.

Device 20 typically includes a flow chamber defined by a tubular housing 26, and an elongate inflatable balloon (not seen) contained therewithin. The balloon communicates via tube 16 with pump 12, whereby a fluid, such as air, may be alternately and recurrently transferred from the pump to the balloon, thus to pump blood through the assist-device chamber.

Referring to FIG. 2, pump 12 generally comprises a bellows 27 having opposed front and rear sides, or walls, 28, 30, respectively, and an expandable pleated tube 32 joined at opposite ends to, and extending between such walls. Walls 28, 30 and tube 32 define a fluid-tight pumping chamber 34 having an inlet/outlet port 36 extending rearwardly therefrom.

Bellows 27 is housed within a cylindrical enclosure 38 having a tubular wall 40 joined at opposite ends to front and rear walls 42, 44, respectively. Enclosure 38 is made of a material allowing magnetic coupling therethrough. The bellows is held within enclosure 38 by securing its rear wall 30 to the enclosure's rear wall 44. Port 36, which projects from wall 30, extends as shown through wall 44, terminating externally in a nipple 36a.

Bellows front wall 28 is relatively movable within enclosure 38 between what will be referred to as compressed and expanded positions, wherein pleated tube 32 is relatively compressed and expanded, respectively.

As wall 28 is moved toward rear wall 30, the volume of chamber 34 decreases—tending to force fluid within chamber 34 out through port 36. As wall 28 is moved away from wall 30, the volume of chamber 34 increases—tending to draw fluid into chamber 34 through port 36. Wall 28 thus defines a movable wall portion, movements of which effect changes in the volume of the pumping chamber.

Pump 12 further includes a drive system, referred to herein as a magnetic driven means, drivingly connected to wall 28 for moving the same. In the embodiment shown, system 49 includes a pair of cylindrical rotary driven members 50, 51 suitably rotatably mounted within enclosure 38 through bearings 52, 54, respectively.

Formed on the cylindrical surfaces of members 50, 51 are grooves 56, 58, respectively, each of which, if viewed in a developed format, would appear with a generally single-wave sinusoidal shape. As can be seen in FIG. 2, these two grooves are arranged on the rotary members in what might be thought of as mirror-image positions. Cooperating with grooves 56, 58 are two cam followers 60, 62, respectively. Each of these followers has a projection which slidably fits within its respective associated groove, and each is suitably guided for reciprocation along a line generally paralleling the rotational axis of the associated rotary member. The left ends of followers 60, 62 in FIG. 2 are suitably connected to the right side of wall 28. With counterrotation of members 50, 51, the production of which will be explained shortly, followers 60, 62 reciprocate in unison to shift wall 28 toward and away from wall 30.

Concentrically attached to the outwardly-facing (right) surface of each of members 50,51 are circular gears 63, 64 dimensioned and positioned to intermesh, whereby rotation of member 50 produces counterrotation of member 51. Each of gears 63, 64 carries on its outwardly-facing surface magnetic pole-defining units 66 arranged to produce a linear array of such poles, as shown in FIG. 4a. This array includes a central subarray having "South" poles 66a near the center of rotation of the associated member, and a peripheral subarray having "North" poles 66b outwardly of the central subarray. In the embodiment shown in FIG. 4a, units 66 are cylindrical permanent magnets suitably oriented to produce the above-desired magnetic polarity.

Pump 12 is actuated by pump driving unit 14, also referred to herein as magnetic driving means, shown in FIG. 3. Unit 14 generally includes, within a cylindrical housing 71, a motor 72, a motor-driven shaft 73, and a pair of rotary driving members 74, 75 supported on shafts 73, 77, respectively, which are journaled by bearings 78, 79, respectively. With reference to FIGS. 3 and 4b, members 74, 75 are formed with peripheral gear teeth which mesh whereby rotation of member 74 produces counterrotation of member 75.

Attached to the outwardly-facing (left in FIG. 3) surface of members 74, 75, are magnetic pole-defining units 82 arranged to produce a linear array of such poles. This array includes a central subarray having "South" poles 82a near the center of rotation of the associated member, and a peripheral subarray having "South" poles 82b disposed outwardly of the central subarray. Units 82 are suitably oriented cylindrical permanent magnets.

Attached to housing 71, and surrounding and enclosing members 74, 75, is a cylindrical cap 71a which is made of a suitable material permitting magnetic coupling therethrough.

It can be appreciated from FIGS. 2 and 3, that with members 74, 75 suitably aligned with members 50, 51, the central subarrays exhibit repulsion and the peripheral subarrays exhibit attraction. Preferably such attraction and repulsion are of about equal magnitude, so that the magnetic coupling between the driving and driven members is rotational, but not translational.

A modified arrangement of magnetic pole-defining units on the driven and driving members disposed in sets of threes, is shown in FIGS. 5a and 5b. Here, pole-defining units 86 attached to the outwardly facing side of each of gears, 63, 64 form a central symmetric subarray having "South" poles 86a near the center of rotation of the associated member, and a peripheral symmetric subarray having "North" poles 86b arranged outwardly of the central subarrays of the member. Similarly, attached to the outwardly facing side of each of members 74, 75 are pole-defining units 90 forming a central subarray having "South" poles 90a near the center of rotation of the associated member, and a peripheral subarray of "South" poles 90b arranged like poles 86b.

The operation of the pump system will now be described, initially with reference to FIG. 1. The heart-assist device shown in FIG. 1 is intended to provide supplemental pumping capacity to a chronically diseased heart. Typically, the device has a 30–40 cc pumping volume, providing about half of the required functioning capacity of the heart.

Pump 12 is surgically implanted in a position where it can be substantially immobilized, and cause minimal interference with body organs. Fluid-transfer tube 16, connected at one end to the heart-assist device, is connected at its other end to pump 12 on nipple 36a. The pump, tube and heart-assist device form a closed fluid system in which fluid is transferable to and from the heart-assist device as the pump is operated.

To operate the pump, driving unit 14 is placed with cap 71a against the outside the body, such that the pump's rotary driven members and unit 14's rotary driving members confront one another.

As the driving unit motor is operated, counterrotating driving members 74, 75 effect, by magnetic coupling across the body surface, counterrotation of rotary driven members 50, 51. Because a substantially equal and opposite torque is applied to each of members 50, 51 by members 74, 75, there is little or no net torque applied to pump 12 during operation. Thus, the tendency of pump 12 to become dislodged is minimized. As described above, rotation of members 50, 51 produces reciprocation of wall 28 through the movement of cam followers 60, 62 tracking in grooves 56, 58, respectively. Because members 50, 51 are rotatably coupled by gears 63, 64, these members counterrotate in synchrony, ensuring that cam followers 60, 62 are longitudinally displaced at the same rate. Locking of members 50, 51, which could occur if one of followers 60, 62 were preferentially displaced, is thereby prevented.

Any conventional technique may be used to coordinate the pumping action produced by the instant system with heart activity.

Thus, a simple, pumping system designed for operation with a body-implanted heart-assist device, which drive is imparted externally and across the surface of the body, has been disclosed. Various modifications and changes in the invention may be made without departing from the true spirit of the invention, as set forth in the appended claims.

It is claimed and desired to secure by Letters Patent:

1. A magnetically driven cardiac-assist pump system comprising
    means defining a changeable-volume pumping chamber including a movable wall portion, movements of which effect changes in the volume of said chamber,
    magnetic driven means drivingly connected to said wall portion for moving the same upon actuation of said driven means, and
    magnetic driving means magnetically couplable with said driven means for actuating the same,
    said driven and driving means comprising rotary members having opposable faces with each carrying means defining an array of magnetic poles, each of said arrays including a central subarray located near the center of rotation of the associated rotary member, and a peripheral subarray located outwardly of said central subarray.
    said central and peripheral subarrays, with said rotary member's faces opposing one another, exhibiting magnetic repulsion and attraction, respectively.

2. A magnetically driven cardiac-assist pump system comprising
    means defining a changeable-volume pumping chamber including a movable wall portion, movements of which effect changes in the volume of said chamber,
    magnetic driven means drivingly connected to said wall portion for moving the same upon actuation of said driven means, and
    magnetic driving means magnetically couplable with said driven means for actuating the same,
    said driven and driving means each comprising a pair of spaced counterrotative members, with said members in said driven means having faces opposable with faces in said members in said driving means, and with each of said faces carrying means defining an array of magnetic poles.

3. A magnetically driven cardiac-assist pump system comprising
    means defining a changeable-volume pumping chamber including a movable wall portion, movements of which effect changes in the volume of said chamber,
    magnetic driven means drivingly connected to said wall portion for moving the same upon actuation of said driven means, and
    magnetic driving means magnetically couplable with said driven means for actuating the same,
    said driven and driving means each comprising a pair of spaced counterrotative members, with said members in said driven means having faces opposable with faces in said members in said driving means, each face carrying means defining an array of magnetic poles,
    each of said arrays including a central subarray located near the center of rotation of the associated member, and a peripheral subarray located outwardly of said central subarray,
    each of said central and peripheral subarrays, with said rotary members' faces opposing one another, exhibiting magnetic repulsion and attraction, respectively.

4. A magnetically driven cardiac-assist pump system comprising
    means defining a changeable-volume pumping chamber including a movable wall portion, movements of which effect changes in the volume of said chamber,
    magnetic driven means drivingly connected to said wall portion for moving the same upon actuation of said driven means, and
    magnetic driving means magnetically couplable with said driven means for actuating the same,
    said driven and driving means each comprising a pair of spaced counterrotative members, with said members in said driving means having faces opposable with faces in said members in said driving means, each face carrying means defining an array of magnetic poles,
    wherein each of said pairs of spaced counterrotative members includes mutually intermeshing gears which counterrotatively couple one member of such pair to the other member.

* * * * *